United States Patent [19]

Muller et al.

[11] Patent Number: 4,908,013

[45] Date of Patent: Mar. 13, 1990

[54] HOLDER FOR A VEIN SEGMENT AND METHOD OF REMOVING CELLS FROM A VEIN SEGMENT

[75] Inventors: Werner Muller, Wiesendangen; Marie-Claude Hensel, Bertschikon; August Huber, Raterschen, all of Switzerland

[73] Assignee: Sulzer Brothers Limited, Winterthur, Switzerland

[21] Appl. No.: 160,160

[22] Filed: Feb. 25, 1988

[30] Foreign Application Priority Data

Mar. 3, 1987 [CH] Switzerland ............................ 825/87

[51] Int. Cl.$^4$ ............................................. A61B 19/00
[52] U.S. Cl. ......................................... 600/36; 435/1; 623/1
[58] Field of Search ....................... 600/36; 623/1, 66; 435/1; 73/38, 40, 45.5; 8/94.11; 206/363, 370, 438; 128/749, 750

[56] References Cited

U.S. PATENT DOCUMENTS

| | | |
|---|---|---|
| 3,459,176 | 8/1969 | Leonard .................................. 604/5 |
| 4,061,134 | 12/1977 | Samuels et al. ........................ 600/36 |
| 4,083,066 | 4/1978 | Shmitz et al. ............................ 623/1 |
| 4,108,161 | 8/1978 | Samuels et al. ........................ 600/36 |
| 4,164,524 | 8/1979 | Ward et al. .............................. 623/1 |
| 4,232,659 | 11/1980 | Dale ......................................... 600/36 |
| 4,473,637 | 9/1984 | Guibert .................................... 435/1 |
| 4,494,385 | 1/1985 | Kuraoka et al. ........................ 435/1 |
| 4,539,716 | 9/1985 | Bell ......................................... 600/36 |
| 4,555,934 | 12/1985 | Freeman et al. ......................... 73/38 |
| 4,736,850 | 4/1988 | Bowman et al. ..................... 206/438 |

Primary Examiner—C. Fred Rosenbaum
Attorney, Agent, or Firm—Kenyon & Kenyon

[57] ABSTRACT

The holder contains a sealed chamber in which a vein segment is clamped centrally with a slight axial pre-stress. For storage and transportation, the interior of the vein segment and the surrounding peripheral portions of the chamber housing the vein segment can be filled with a physiological common salt solution via flow channels. For removal of endothelial cells, an enzyme solution can be passed through the flow channels aligned with the vein segment to entrain the endothelium cells therein for subsequent processing.

20 Claims, 2 Drawing Sheets

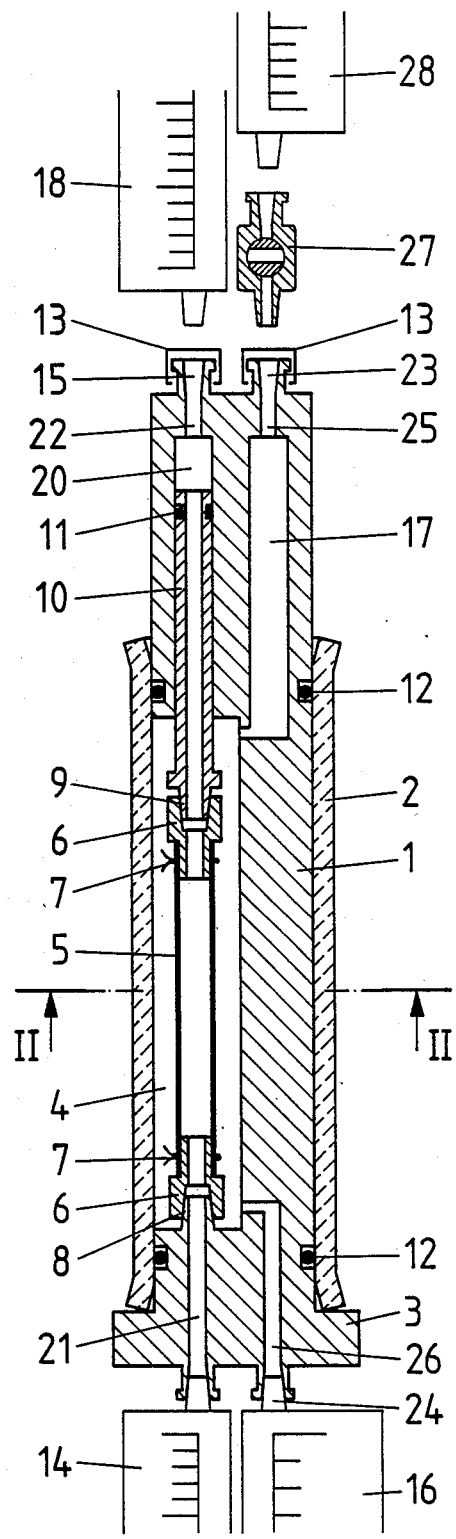
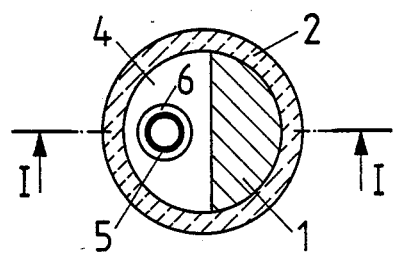
Fig. 1
Fig. 2

Fig. 3
Fig. 4
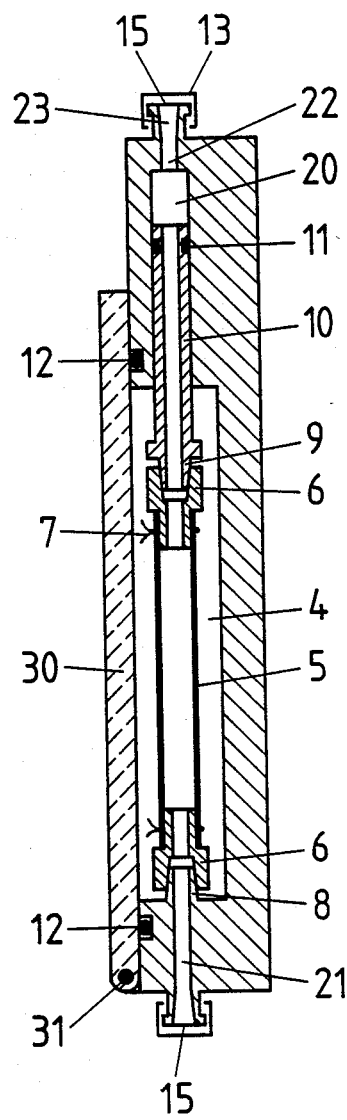
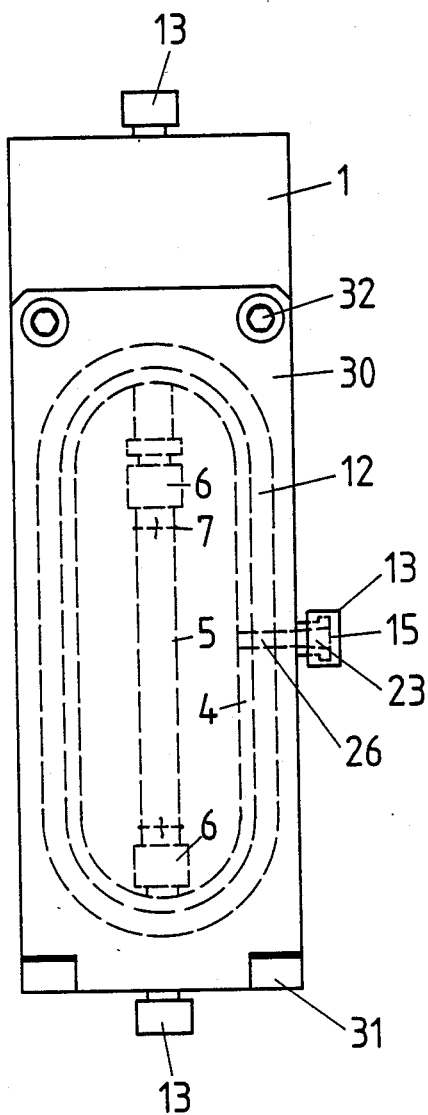

HOLDER FOR A VEIN SEGMENT AND METHOD OF REMOVING CELLS FROM A VEIN SEGMENT

This invention relates to a holder for a vein segment and to a method of removing cells from a vein segment. More particularly, this invention relates to a holder for storing and/or treating surgically obtained vein segments and to a method of obtaining cells from the vein segment for cell growth culture.

Heretofore, in vessel transplantations, it may sometimes be necessary to temporarily store a vein segment which has been surgically removed from an extremity such as an arm or a leg, outside the body. However, care must be taken that the vein segment which has been detached does not shrink. Further, care must be taken the that vein segment is not stretched or extended when or before reinserted. In either case, high stresses and damage may occur to the living cells contained in the vein segment.

Further, it has been known that in the case of alloplastic vessel prostheses for small vessels having an inside diameter of, for example, at most six millimeters, the formation of thrombi can be prevented in a lasting manner only if the alloplastic prosthesis is coated internally with patient-specific (autologous) epithelium, i.e. endothelium, cells. In order to obtain such patient-specific cells, various techniques have been employed.

For example, in order to obtain patient-specific cells, during a first operation and under local anesthesia, a piece of surface vein of a length adapted to the anatomical situation and which may, for example, be approximately five centimeters in length is taken from the patient at a suitable point, for example on the lower arm. The excised vessel segment is taken from the operating room to a suitable biomedical laboratory. There the endothelium cells are detached from the inside of the vein segment, multiplied in a cell growth culture and thereafter applied on the inside of an artificial prosthesis, i.e. artificial vessel. This artificial vessel having been lined with the patient-specific endothelium cells is then implanted in the patient in a second operation, i.e. The main operation.

This cell multiplication process, however, is extremely difficult. Therefore, the more living cells that are obtained from the vein segment at the beginning, the better will be the initial growth conditions and the fewer the multiplication steps will be needed to obtain the required final quantity of living cells. Consequently, cell recovery must be carried out under optimum conditions.

In principle, two methods are currently used for obtaining endothelium cells from a blood vessel, in this case, from a vein segment.

In one method, the so-called cannulation method, a needle of suitable diameter is introduced into a vein segment at both ends the and the segment is fixed in the cannulae by means of ligatures, i.e. by tying. Next, the vein segment is rinsed with physiological common salt solution to remove blood residues. Next, a defined enzymatic solution of collagenase or a collagenase/trypsin mixture is filled in. The two cannulae are then sealed or closed and the vein segment placed in a Petri dish filled with common salt solution. The vein segment remains in the dish for a given period at a temperature which approximately corresponds to the body temperature of about 37° C. In order to support the detachment of cells, the vein segment may be carefully massaged from the outside from time to time with the fingers. A cell "sediment" is obtained by centrifuging the solution washed out of the vessel. From this sediment, the living endothelium cells intended for multiplication are obtained by resuspension in a suitable culture medium of the growth culture.

In the second method, the so-called eversion method, the excised vein segment is slipped at one end onto a glass rod over a short length and fixed by ligature. Then, the entire vein segment is everted so that the inside is turned out over the glass rod. The cells can then be obtained either by scrapping, without the use of enzymes, using a suitable miniature scrapper (rubber policemen) or by immersing the everted vein in an enzyme solution—again collagenase or collagenase/trypsin mixture—stored at 37° C. for a given time and then scrapped off with the same scrapper. Another possibility is to use the same technique but replacing mechanical scrapping by spraying with a liquid.

Generally speaking, cannulation is a gentler method than eversion. By everting the vein segment some damage to the cells is inevitable. If scrapping is used, it is to be expected that the tissue layers under the endothelium cells will be damaged. This will then lead to extremely undesirable contaminations of the cell culture with foreign cell types, for example, fibroblasts or smooth muscle cells.

Accordingly, it is an object of the invention to permit a cell-protecting storage of surgically removed vein segments.

It is another object of the invention to provide a means by which as many living and viable endothelium cells as possible can be obtained from a vein segment.

It is another object of the invention to provide a simple apparatus for storing and transporting a vein segment.

Briefly, the invention provides a holder for a vein segment which comprises a base having a chamber for receiving a vein segment, a removable closure element mounted on the base to close the chamber and a vein segment holding and tensioning means disposed in the chamber for mounting a vein segment therein. In addition, the holder includes a pair of flow channels for communicating the interior of a mounted vein segment with the exterior of the base for passage of fluid therebetween as well as a third flow channel communicating a periphery of the chamber with the exterior of the base.

The base is made of a biologically inert material and the chamber is positioned so as to be readily accessible from the outside when the closure element is removed. In addition, the closure element is hermetically sealed with respect to the base when in place, for example via suitable seals. The holding and tensioning means is constructed so as to mount the vein segment in a longitudinally tensioned state. In addition, the device is longitudinally adjustable in order to adjust to different lengths of vein segments.

The flow channels which communicate with the holding and tensioning means are disposed in the base in alignment with a mounted vein segment so that a fluid solution may be filled into the interior of the vein segment and/or flushed therethrough.

The flow channel which communicates with the periphery of the chamber may also have an evacuable buffer space for a fluid in order to provide for pressure equalization on the walls of the vein segment.

The invention also provides a method for mounting and transporting the vein segment as well as for removing cells from the mounted vein segment. In this respect, the vein segment is mounted under longitudinal tension in the sealed chamber of the holder with the opposite ends of the segment communicating with the means for passing a flushing solution therethrough. In accordance with the method, the solution is flushed through the vein segment to remove blood residue and to subsequently fill the interior of the vein segment for storage and transportation purposes. In addition, the chamber is filled about the vein segment with a physiological common salt solution to prevent drying of the vein segment while the buffer space has an air cushion therein to define a pressure equalization vessel.

A vacuum may also be created in the pressure equalization vessel to radially extend the vein segment a slight amount in the sealed chamber so as to prevent collapse of the vein segment.

After transportation of the vein segment to a laboratory or other suitable site, the flushing solution is evacuated from within the vein. Thereafter, the vein segment is filled with an enzyme solution and the solution moved therein to entrain cells from within the vein segment. Finally, the cell-entrained enzyme solution is removed while retaining the vein segment in the holder. The removed solution can then be processed in a conventional manner so as to obtain the entrained cells.

The method utilizes cannulation techniques in order to obtain the cells from the vein segment. This technique offers very simple handling which is an advantage not to be underestimated when working under sterile conditions. Further, the overall method permits a reproducable very high cell yield. For example, up to 90% of the endothelium cells contained in a vein segment may be obtained.

In one embodiment, the base is of circular cylindrical shape with each flow channel terminating in a respective end face. In addition, the chamber opens laterally, that is, is accessible through the generated surface of the circular cylinder. The closure element is then in the form of a sleeve and, particularly, a transparent sleeve, that can be axially slipped onto the base. In this respect, the base may be provided at one end face with a shoulder to act as a stop for the slipped-on sleeve.

In another embodiment, the base may be of rectangular shape with the closure element in the form of a plate.

These and other objects and advantages of the invention will become more apparent from the following detailed description taken in conjunction with the accompanying drawings wherein:

FIG. 1 illustrates a cross sectional view taken on line I—I of FIG. 2 of a holder constructed in accordance with the invention;

FIG. 2 illustrates a view taken on line II—II of FIG. 1;

FIG. 3 illustrates a cross sectional view of a modified holder constructed in accordance with the invention; and FIG. 4 illustrates an exterior view of the holder of FIG. 3.

Referring to FIG. 1, the holder is constructed of a circular cylindrical base 1 of a biologically inert material and a closure element in the form of a transparent sleeve 2 which is mounted on the base in hermetically sealed relation. As indicated, the base 1 has a shoulder 3 at the lower end which functions as a stop for the transparent sleeve 2 as well as for fixation to a mounting (not shown). In addition, the base 1 has a chamber 4 for receiving vein segment 5. As indicated in FIG. 2, the vein chamber 4 is recessed in the base 1 and is laterally accessible i.e the base 1 has a pair of end walls defining the recessed chamber.

The vein chamber 4 is sized so as to receive a vein segment 5 via a holding and tensioning means (device) which includes a pair of hollow connectors 6 for engaging within opposite ends of the vein segment 5. A ligature 7, for example of surgical suture material, is used to secure the vein segment 5 to each connector 6. Each connector 6 also has a conical inner bore which is fitted onto a corresponding male cone 8, 9. As viewed, the lower cone 8 is firmly connected with the base 1 or is a part of the base 1. The cone 9 is formed at one end of an elongated tube 10 which is slidably mounted in a longitudinal channel 20 in the base 1.

The holding and tensioning means is longitudinally adjustable to adjust to different lengths of vein segments. To this end, the free length between the connectors 6 can be adapted to the length of the vein segment 5. As the vein segment 5 should be extended to its original length in the body before being removed, the segment 5 is tensioned when mounted in the base 1 via the tube 10.

An O-ring 11 is provided on the tube 10 to serve as a seal and simultaneously to hold the tube 10 with a friction fit within the channel 20.

A pair of O-rings 12 in the base 1 serve to hermetically seal the sleeve 2 in place.

A pair of flow channels 21, 22 are provided in the base 1 to communicate the chamber 4 with the exterior of the base 1. The lowermost channel 21 terminates at one end in the cone 8 and at the opposite end in a spigot which projects from the bottom of the base 1. The upper flow channel 22 terminates at one end with the channel 20 and at the opposite end in a spigot which extends from the base 1. As illustrated, the spigots extending from the base 1 each have a female cone 15 shaped to matingly receive an end of a commercially available syringe 14, 18. In addition, a removable cap 13 is provided on each spigot for closure purposes.

A pair of additional flow channels 25, 26 are disposed in the base 1 to communicate a periphery of the vein chamber 4 with the exterior of the base 1. Each of these flow channels 25, 26 terminates in an opposite end face of the base 1 within a spigot having a female cone 23 adapted to receive a counter-cone 24 of an injection syringe 16, 28. Suitable caps 13 are also provided for the spigots, for example in the form of rotary closures.

As indicated in FIG. 1, an evacuable buffer space 17 is provided in the flow channel 25 for purposes as described below.

In addition, a shut-off valve 27 may also be mounted in the spigot communicating with the flow channel 25.

Mounting of a vein segment 5 secured on the connectors 6 is performed with the sleeve 2 pulled off the base 1. In this respect, the tube 10 is slid into the longitudinal channel 20 and the lower connector 6 is mounted on the cone 8. Depending upon the amount of tension desired, the tube 10 is slid into the channel 20 more or less.

After placement of the vein segment 5 in the chamber 4, for example under a light axial prestress, the transparent sleeve 2 is slid over the chamber 4 with the two seal rings 12 bringing about a gas-tight closure and protecting the chamber 4 against contamination.

After closing the chamber 4, the caps 13 on the flow channels 21, 22 which are aligned with the tube 10 and vein segment 5 are opened and a commercial syringe 14 or other means is attached to the channel 21. A flushing solution is then passed through the vein segment 5 in a vigorous manner until no blood residues remain. This solution which is physiological common salt solution may then fill the vein segment 5 to act as a preservative which remains inside the vein segment 5 when the syringe 14 has been removed and the caps 13 placed over the openings 15. Thereafter, the caps 13 are removed or opened to clear the flow channels 25, 26 and by means of a conventional syringe 16 which is attached to the flow channel 26, the chamber about the vein segment 5 can be filled with a physiological common salt solution to prevent drying of the vein segment. However, an air cushion is retained with the buffer space 17 so that this space acts as a pressure equalization vessel. Prolonged collapse of the vein segment 5 is thus prevented as, otherwise, a collapse would lead to damage to the living endothelium cells to be obtained.

If the vein segment 5 is to be extended somewhat more in the radial direction, a slight vacuum may be formed in the space 17 by an additional syringe 28 which is attached to the end of the flow path 25 via the shut-off valve 27.

After filling of the peripheral vein chamber 4 with common salt solution, the openings to the flow paths 25, 26 are again closed via the caps 13 while retaining the vacuum in the space 17. Thereafter, the holder can be placed in a packing (not shown) which ensures sterility and the entire apparatus transported to a laboratory for recovery of the endothelium cells.

The recovery of the endothelium cells may occur, for example, as follows.

The caps 13 are removed from the flow channels 21, 22 and the flushing or preservative liquid is evacuated. If, in so doing, even a brief collapse of the vein segment 5 is to be prevented, a vacuum is created or intensified in the peripheral region of the chamber 4. The vein segment 5 is then filled with an enzyme solution by means of an additional syringe 14 via the flow channel 21 and synchronizally moved back and forth with a syringe 18 connected to the flow path 22. By build up of a slight positive pressure inside the vein segment 5, the vein segment 5 is expanded, for example by two to three percent of the original diameter. The liquid displaced from the chamber 4 is then able to flow into the buffer space 17. Experimental tests have shown that by synchronized moving of the two syringes 14, 18, the cell yield is considerably increased. This process replaces the previously described massaging of the vein segment 5 from outside and assures that the endothelium cells detached from their substrate are entrained by the occurring flow forces but are not damaged. After removal of the syringe 18, the enzyme solution with the entrained endothelium cells is drawn into the syringe 14. Because of this protective procedure, the endothelium cells which are obtained are practically free from foreign cells, such as fibroblasts or smooth muscle cells.

Referring to FIGS. 3 and 4, wherein like reference characters indicate like parts as above, the holder may have a base 1 constructed of rectangular form while the closure element is in the form of a flat plate 30. As indicated, the plate 30 may be mounted via a hinge 31 to the base 1 and secured in placed via suitable bolts 32. In addition, a seal 12 can be disposed in the base 1 to hermetically seal against the plate 30 when in place.

As indicated in FIG. 3, a pair of flow channels 21, 22 are disposed in the base 1 to communicate with the interior of the vein segment 5 while, as shown in FIG. 4, a third flow channel 26 is provided to communicate with the periphery of the vein chamber 4 about the vein segment 5.

The remainder of the construction of the holder is analogous to the holder described with respect to FIGS. 1 and 2. As is know, as all vessels in the human or animal body are lined internally with a specific layer of epithelium cells, the holder may be useful for the recovery of these other epithelium cells as well as endothelium cells.

The invention thus provides a relatively simple holder for storage and transportation of a vein segment which has been excised from a patient.

Further, the invention provides a vein segment holder which can be readily used in a method of removing endothelium cells and the like from a vein segment utilizing a cannulation technique.

What is claimed is:

1. A holder for a vein segment comprising
   a base having a pair of end walls defining a laterally accessible recessed chamber for receiving a vein segment;
   a closure element mounted on said base in hermetically sealed relation to close said chamber;
   a pair of flow channels each flow channel being disposed in a respective wall of said base and communicating said chamber with the exterior of said base;
   a vein segment holding and tensioning means disposed in said chamber for mounting a vein segment between and in communication with said flow channels for passage of fluid therebetween; and
   at least a third flow channel in said base communicating a periphery of said chamber with the exterior of said base.

2. A holder as set forth in claim 1 wherein said vein holding and tensioning means is longitudinally adjustable to adjust to different lengths of vein segments.

3. A holder as set forth in claim 1 which further comprises an evacuable buffer space for a fluid in at least one of said flow channels.

4. A holder as set forth in claim 1 wherein said base is of circular cylindrical shape with each flow channel terminating in a respective end wall thereof and wherein said chamber opens laterally of said base.

5. A holder as set forth in claim 1 wherein said closure element is a plate.

6. A holder as set forth in claim 1 wherein said vein holding and tensioning means includes a pair of hollow connectors for engaging within opposite ends of vein segment and for mounting within said chamber in communication with said pair of flow channels.

7. A holder as set forth in claim 1 wherein said base is of biologically inert material.

8. A holder for a vein segment comprising
   a base having a pair of end walls defining a laterally accessible recessed chamber for receiving a vein segment;
   removable closure element mounted on said base to close said chamber;
   a vein segment holding and tensioning means disposed in said chamber for mounting a vein segment in tensioned relation thereon;
   a pair of flow channels for communicating an interior of a vein segment mounted on said holder and tensioning means with the exterior of said base for passage of fluid therebetween each flow channel being disposed in a respective wall of said base; and a third flow channel communicating a periphery of said chamber with the exterior of said base.

9. A holder as set forth in claim 8 wherein said vein holding and tensioning means includes a pair of hollow connectors for engaging within opposite ends of a vein segment and for mounting within said chamber in communication with said pair of flow channels.

10. A holder as set forth in claim 9 wherein said means includes an elongated tube receiving one of said connectors thereon in axial alignment and being slidably mounted in said base in communication with one of said pair of flow channel.

11. A holder as set forth in claim 8 which further comprises an evacuable buffer space for a fluid in at least one of said flow channels.

12. A holder as set forth in claim 8 wherein said closure element is transparent.

13. In a method of removing cells from a vein segment, the steps comprising
mounting the vein segment under longitudinal tension in a sealed chamber;
communicating the opposite ends of the vein segment with a means for passing a flushing solution therethrough;
flushing the solution through the vein segment to remove blood residue;
filling the chamber about the vein segment with a physiological common salt solution to prevent drying of the vein segment; and
communicating the periphery of the chamber with a buffer space having an air cushion therein to define a pressure equalization vessel.

14. In a method as set forth in claim 13, the steps of creating a vacuum in said pressure equalization vessel to radially extend the vein segment in said chamber.

15. In a method as set forth in claim 13, the steps of evacuating the flushing solution within the vein;
thereafter filling the vein segment with an enzyme solution and moving the enzyme solution therein to entrain cells from within the vein segment; and
removing the cell-entrained enzyme solution while retaining the vein segment in the holder.

16. A holder for a vein segment comprising
a base of circular cylindrical shape having a chamber for receiving a vein segment opening laterally of said base, said base having a shoulder at one end;
a closure element abutting said shoulder and mounted on said base in hermetically sealed relation to close said chamber;
a pair of flow channels in said base communicating said chamber with the exterior of said base, each said flow channel terminating in a respective end face of said base;
a vein segment holding and tensioning means disposed in said chamber for mounting a vein segment between and in communication with said flow channels for passage of fluid therebetween; and
at least a third flow channel in said base communicating a periphery of said chamber with the exterior of said base.

17. A holder for a vein segment comprising
a base of circular cylindrical shape having a chamber for receiving a vein segment opening laterally of said base;
a sleeve mounted on said base in hermetically sealed relation to close said chamber;
a pair of flow channels in said base communicating said chamber with the exterior of said base, each said flow channel terminating in a respective end face of said base;
a vein segment holding and tensioning means disposed in said chamber for mounting a vein segment between and in communication with said flow channels for passage of fluid therebetween; and
at least a third flow channel in said base communicating a periphery of said chamber with the exterior of said base.

18. A holder for a vein segment comprising
a base having a chamber for receiving a vein segment;
a closure element mounted on said base in hermetically sealed relation to close said chamber;
a pair of flow channels in said base communicating said chamber with the exterior of said base;
a vein segment holding and tensioning means disposed in said chamber for mounting a vein segment between and in communication with said flow channels for passage of fluid therebetween;
a pair of spigots, each spigot terminating each respective flow channel and having a cone-shaped bore for matingly receiving an end of a syringe;
a pair of caps, each said cap being removably mounted on a respective spigot; and
at least a third flow channel in said base communicating a periphery of said chamber with the exterior of said base.

19. A holder as set forth in claim 18 wherein each spigot has a cone-shaped bore for matingly receiving an end of a syringe.

20. A holder for a vein segment comprising
a base having a chamber for receiving a vein segment;
a closure element mounted on said base in hermetically sealed relation to close said chamber;
a pair of flow channels in said base communicating said chamber with the exterior of said base;
a vein segment holding and tensioning means disposed in said chamber for mounting a vein segment between and in communication with said flow channels for passage of fluid therebetween, said means including a pair of hollow connectors for engaging with opposite ends of a vein segment and a pair of elongated tubes, each said tube receiving one of said connectors thereon in axial alignment and being slidably mounted in said base in communication with a respective one of said flow channels; and
at least a third flow channel in said base communicating a periphery of said chamber with the exterior of said base.

* * * * *

UNITED STATES PATENT AND TRADEMARK OFFICE
CERTIFICATE OF CORRECTION

PATENT NO. : 4,908,013

DATED : March 13, 1990

INVENTOR(S) : WERNER MULLER, et al

It is certified that error appears in the above-identified patent and that said Letters Patent is hereby corrected as shown below:

```
Column 1, line 17 "the that vein" should be -that the vein-
Column 1, line 18 "before reinserted" should be -before being
      reinserted-
Column 1, line 34 "example on" should be -example, on-
Column 1, line 35 "is taken" should be -is then taken-
Column 1, line 42 "The" should be -the-
Column 1, line 57 "ends the and the segment" should be -ends and
      the segment-
Column 5, line 62 "placed" should be -place-
Column 6, line 5  "know" should be -known-
Column 6, line 24 "channels each" should be -channels, each-
Column 6, line 50 "of vein" should be -of a vein-
Column 6, line 67 "therebetween each" should be -therebetween,
      each-
Column 7, line 13 "channel" should be -channels-
```

Signed and Sealed this

Thirtieth Day of July, 1991

Attest:

HARRY F. MANBECK, JR.

*Attesting Officer*   *Commissioner of Patents and Trademarks*